US006872737B2

(12) United States Patent
Gil et al.

(10) Patent No.: US 6,872,737 B2
(45) Date of Patent: Mar. 29, 2005

(54) HETEROCYCLIC INHIBITORS OF GLYCOGEN SYNTHASE KINASE GSK-3

(75) Inventors: Ana Martinez Gil, Madrid (ES); Ana Castro Morera, Madrid (ES); Maria Concepcion Martin Perez, Madrid (ES); Mercedes Alonso Cascon, Madrid (ES); Isabel Dorronsoro Diaz, Madrid (ES); Francisco Jose Moreno Munoz, Madrid (ES); Francisco Wandosell Jurado, Madrid (ES)

(73) Assignee: Consejo Superior de Investigaciones Cientificas (ES)

( * ) Notice: Subject to any disclaimer, the term of this patent is extended or adjusted under 35 U.S.C. 154(b) by 0 days.

(21) Appl. No.: 10/290,569

(22) Filed: Nov. 8, 2002

(65) Prior Publication Data

US 2003/0195238 A1 Oct. 16, 2003

Related U.S. Application Data

(63) Continuation-in-part of application No. PCT/GB01/02100, filed on May 11, 2001.

(30) Foreign Application Priority Data

| May 11, 2000 | (ES) | 200001185 |
|---|---|---|
| Dec. 12, 2000 | (GB) | 0030284 |

(51) Int. Cl.$^7$ .................. A61K 31/41; C07D 285/08; A61P 31/00
(52) U.S. Cl. .................. 514/361; 514/351; 548/128; 548/129
(58) Field of Search .................. 548/129, 128; 514/361, 359

(56) References Cited

U.S. PATENT DOCUMENTS

| 3,374,240 A | 3/1968 | Ottman et al. |
|---|---|---|
| 3,534,057 A | 10/1970 | Krenzer |
| 3,900,485 A | 8/1975 | Krenzer |
| 4,183,816 A | * 1/1980 | Gavin et al. ............ 508/272 |

FOREIGN PATENT DOCUMENTS

| DE | 4420522 | * 12/1995 | |
|---|---|---|---|
| EP | 0 711 773 A1 | 5/1996 | C07D/487/04 |
| JP | 58216177 | 12/1983 | |
| WO | WO 95/17182 | 6/1995 | A61K/31/40 |
| WO | WO 00/21927 | 4/2000 | C07D/207/00 |
| WO | WO 00/38675 | 7/2000 | A61K/31/40 |
| WO | WO 01/09106 A1 | 2/2001 | C07D/249/14 |

OTHER PUBLICATIONS

Jha et al., 1998, "Donor behavior of isoperthiocyanic acid..", CAS:128:96805.*
Groutas et al., 1994, "Substituted 3–oxo–1,2,5–thiadiazolidine 1, 1–dioxides..", CAS:120:124451.*
Marcinkeviciene et al. , 2000, Biochemical Pharmacology, "Selective inhibition of bacterial dihydroorotate..", 60:339–342.*
Heuer et al., 1996, "Bactericidal thiadiazolidinedione.", CAS:124:48317.*
English–translated version of DE 4420522, and a comment from USPTO Germanic language translator, dated May 4, 2004.*
Martinez et al., "Synthesis and Potential Muscarinic Receptor Binding and Antioxidant Properties of 3–(Thiadiazolyl)pyridine 1–Oxide Compounds" *Arch. Pharm. Pharm. Med. Chem.*, vol. 332,pp. 191–194 (1999).
Martinez et al., "Arylimino–1,2,4–Thiadiazolidinones: A New Family of Potassium Channel Openers", *Bioorganic & Medicinal Chemistry*, vol. 5, No. 7, pp. 1275–1283 (1997).
Slomczynska et al., "Efficient Synthesis of 1,2,4—Dithiazolidine–3,5–diones (Dithiasuccinoyl–amines) and Observation on Formation of 1,2,4—Thiadiazolidine–3,5–diones by Related Chemistry", *J. Heterocyclic Chem.*, vol. 21, pp. 241–246 (1984).
STN Registry No.: 89570–37–6.

* cited by examiner

*Primary Examiner*—Joseph K. McKane
*Assistant Examiner*—Robert Shiao
(74) *Attorney, Agent, or Firm*—Fish & Richardson PC

(57) ABSTRACT

Compounds of general formula (I):

$$\underset{G\text{---}E}{X=\overset{A}{\diagup\hspace{-0.3em}\diagdown}=Y}$$ (I)

where A, E, G, X, Y and the bond - - - take various meanings are of use in the preparation of a pharmaceutical formulation, for example in the treatment of a disease in which GSK-3 is involved, including Alzheimer's disease or the non-dependent insulin diabetes mellitus, or hyperproliferative disease such as cancer, displasias or metaplasias of tissue, psoriasis, arteriosclerosis or restenosis.

25 Claims, No Drawings

HETEROCYCLIC INHIBITORS OF GLYCOGEN SYNTHASE KINASE GSK-3

CROSS-REFERENCE TO RELATED APPLICATION

This application is a continuation-in-part and claims the benefit of priority under 35 USC 120 of international application serial no. PCT/GB01/02100, filed May 11, 2001. The disclosure of the prior application is considered part of and is incorporated by reference in the disclosure of this application. This application also is a continuation-in-part and claims the benefit of priority under 35 USC 119 of Spanish application serial number ES 200001185, filed May 11, 2000, and United Kingdom application serial number GB 0030284.4, filed Dec. 12, 2000.

FIELD OF THE INVENTION

The present invention relates to enzyme inhibitors, and more particularly to heterocyclic inhibitors of glycogen synthase kinase 3β, GSK-3.

BACKGROUND OF THE INVENTION

Alzheimer's disease (AD) is a neurodegenerative process characterised by cognitive disorders associated with a progressive deterioration of the cholinergic function, and neuropathological lesions as senile plaques, formed by the fibrillary β-amyloid, and neurofibrillary tangles, bundles of paired helical filaments.

Generally speaking, AD is restricted to groups aged 60 years or more and is the most common cause of dementia in the elderly population. Today, AD affects 23 million people worldwide. As longevity increases, it is estimated that by the year 2050 the number of cases of AD will more than triplicate [Amaduci, L.; Fratiglioni, L. "Epidemiology of AD: Impact on the treatment", in *Alzheimer Disease: Therapeutic Strategies*, E. Giacobini and R. Becker, Eds., Birhauser, EEUU, 1994, pp. 8].

Two major histological lesions are observed in AD brains associated with the neuronal loss: neurofibrillary tangles and senile plaques at the intracellular and extracellular level respectively ["Alzheimer Disease: From molecular biology to therapy", E. Giacobini and R. Becker, Eds., Birhauser, EEUU, 1996].

Neurofibrillary tangles are structures formed by paired helical filaments (PHFs). They are comprised mainly of the microtubule-associated protein (MAP) tau in an abnormally hyperphosphorylated state [Grundke-Iqbal, I.; Iqbal, K.; Tung, Y. C.; Quinlan, M.; Wisniewski, H. M.; Binder, L. I., "Abnormal phosphorylation of the microtubule-associated protein tau in Alzheimer cytoskeletal pathology", *Proc. Natl. Acad. Sci. USA*, 1986, 83, 4913–4917; Grundke-Iqbal, I.; Iqbal, K.; Quinlan, M.; Tung, Y. C.; Zaidi, M. S.; Wisniewski, H. M., "Microtubule-associated protein tau. A component of the Alzheimer paired helical filaments", *J. Biol. Chem.*, 1986, 261, 6084–6089; Greenberg, S. G.; Davies, P.; Schein, J. D.; Binder, L. I., "Hydrofluoric acid-treated tau PIIF proteins display the same biochemical properties as normal tau.", *J. Biol. Chem.*, 1992, 267, 564–569]. Such aberrant phosphorylation of tau, determined by the effects of different protein kinases and phosphatases, appears to compromise on its ability to bind to and stabilise microtubules and this may contributes to AD pathology [Moreno, F. J.; Medina, M.; Perez, M.; Montejo de Garcini, E.; Avila, J., "Glycogen sintase kinase 3 phosphorylation of different residues in the presence of different factors: Analysis on tau protein", *FEBS Lett.*, 1995, 372, 65–68]. Thus, the blockade of this hyperphosphorylation step may be a prime target at which to interrupt the pathogenic cascade. The selective inhibitors of tau kinases might be new effective drugs for the treatment of AD.

The search for tau kinases inhibitors is a field of a great interest. Tau can be phosphorylated by several proline-directed protein kinases (PDKs) and non-PDKs. However, in AD the exact role of any of these kinases in the abnormal hyperphosphorylation of tau is not yet understood and to date, the activity of these kinases has not been found to be upregulated. It is no doubt that glycogen synthase kinase 3β (GSK-3β) is an in vivo tau kinase in the brain [Lovestone, S.; Hartley, C. L.; Pearce, J.; Anderton, B. H., "Phosphorylation of tau by glycogen synthase-3 in intact mammalian cells: the effects on the organization and stability of microtubules", *Neuroscience*, 1996, 73, 1145–1157; Wagner, U.; Utton, M.; Gallo, J. M.; Miller, C. C., "Cellular phosphorylation of tau by GSK-3β influences tau binding to microtubules and microtubule organisation", *J. Cell. Sci.*, 1996, 109, 1537–1543; Ledesma, M.; Moreno, F. J.; Perez, M. M.; Avila, J., "Binding of apolipoprotein E3 to tau protein: effects on tau glycation, tau phosphorylation and tau-microtubule binding, in vitro", *Alzheimer Res.*, 1996, 2, 85–88]. These findings open the gate to the use of GSK-3, inhibitors as therapeutical agents in the treatment of AD. At the moment few compounds are known with this enzymatic inhibitory property.

Lithium behaves as a specific inhibitor of the GSK-3 family of protein kinases in vitro and in intact cells Muñoz-Montaño, J. R.; Moreno, F. J.; Avila, J.; Diaz-Nido, J., "Lithium inhibits Alzheimer's disease-like tau protein phosphorylation in neurons", *FEBS Lett.*, 1997, 411, 183–188].

Finally, it is observed that insulin inactivates GSK-3 and it is shown that the non-dependent insulin diabetes mellitus is developed with the activation of this enzyme. So that, GSK-3 inhibitors would be a new therapy for the non-dependent insulin diabetes mellitus.

In our work team we have recently discovered a new family of small synthetic heterocyclic molecules with GSK-30 inhibitory properties at micromolar level.

DESCRIPTION OF THE INVENTION

The invention is directed to the compounds represented by the general formula I:

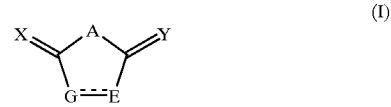

(I)

where:
A is —C($R^1$)$_2$—, —O— or —N$R^1$—;
E is —N$R^1$— or —C$R^1R^2$— and the substituent $R^2$ is absent if - - - is a second bond between E and G;
G is —S—, —N$R^1$— or —C$R^1R^2$— and the substituent $R^2$ is absent if - - - is a second bond between E and G;
- - - may be a second bond between E and G where the nature of E and G permits and E with G optionally then forms a fused aryl group;
$R^1$ and $R^2$ are independently selected from hydrogen, alkyl, cycloalkyl, haloalkyl, aryl, —(Z)$_n$-aryl, heteroaryl, —O$R^3$, —C(O)$R^3$, —C(O)O$R^3$, —(Z)$_n$—C(O)O$R^3$ and —S(O)$_r$— or as indicated $R^2$ can be such that E with G then form a fused aryl group;

Z is independently selected from —C($R^3$)($R^4$)—, —C(O)—, —O—, —C(=N$R^3$)—, —S(O)$_t$—, N($R^3$)—;

n is zero, one or two;

t is zero, one or two;

$R^3$ and $R^4$ are independently selected from hydrogen, alkyl, aryl and heterocyclic; and X and Y are independently selected from =O, =S, =N($R^3$) and =C($R^1$)($R^2$).

DETAILED DESCRIPTION OF THE INVENTION

As used in this specification and appended claims, unless specified to the contrary, the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents independently selected from the group consisting of a halo, hydroxy, alkoxy, carboxy, cyano, carbonyl, acyl, alkoxycarbonyl, amino, nitro, mercapto and alkylthio.

"Alkoxy" refers to a radical of the formula —O$R_a$ where $R_a$ is an alkyl radical as defined above, e.g., methoxy, ethoxy, propoxy, etc.

"Alkoxycarbonyl" refers to a radical of the formula —C(O) O$R_a$ where $R_a$ is an alkyl radical as defined above, e.g., methoxycarbonyl, ethoxycarbonyl, propoxycarbonyl, etc.

"Alkylthio" refers to a radical of the formula —S$R_a$ where $R_a$ is an alkyl radical as defined above, e.g., methylthio, ethylthio, propylthio, etc.

"Amino" refers to a radical of the formula —NH$_2$.

"Aryl" refers to a phenyl or naphthyl radical, preferably a phenyl radical. The aryl radical may be optionally substituted by one or more substituents selected from the group consisting of hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Acyl" refers to a radical of the formula —C(O)—$R_c$ and —C(O)—$R_d$ where $R_c$ is an alkyl radical as defined above and $R_d$ is an aryl radical as defined above, e.g., acetyl, propionyl, benzoyl, and the like.

"Aroylalkyl" refers to an alkyl group substituted with —C(O)—$R_d$. Preferred examples include benzoylmethyl.

"Carboxy" refers to a radical of the formula —C(O)OH.

"Cyano" refers to a radical of the formula —CN

"Cycloalkyl" refers to a stable 3- to 10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more substituents independently selected from the group consisting of alkyl, halo, hydroxy, amino, cyano, nitro, alkoxy, carboxy and alkoxycarbonyl.

"Fused aryl" refers to an aryl group, especially a phenyl or heteroaryl group, fused to the five-membered ring.

"Halo" refers to bromo, chloro, iodo or fluoro.

"Haloalkyl" refers to an alkyl radical, as defined above, that is substituted by one or more halo radicals, as defined above, e.g., trifluoromethyl, trichloromethyl, 2,2,2-trifluoroethyl, 1-fluoromethyl-2-fluoroethyl, and the like.

"Heterocycle" refers to a heterocyclyl radical. The heterocycle refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran. The hetrocycle may be optionally substituted by $R^3$ and $R^4$ as defined above in the summary of the invention.

"Heteroaryl" refers to an aromatic heterocycle

"Mercapto" refers to a radical of the formula —SH

"Nitro" refers to a radical of the formula —NO$_2$

The invention is in particular directed to the enzymatic activity against kinases of the compounds of the general formula I.

A is preferably selected from —C($R^1$)$_2$— and —N$R^1$—.

Preferably $R^1$ is selected from hydrogen, alkyl, cycloalkyl, aryl (optionally substituted with a group selected from alkyl, halo and alkoxy), —C($R^3$)($R^4$)-aryl (the aryl part being optionally substituted with a group selected from alkyl, halo and alkoxy), —O$R^3$, —C(O)O$R^3$ and —C($R^3$)($R^4$)—C(O)O$R^3$, and $R^3$ and $R^4$ are independently selected from hydrogen and alkyl.

The subscript n is preferably zero or one, and n will be chosen having regard to the known chemistry of possible groupings.

X and Y are preferably oxygen or sulphur, at least one of X and Y is preferably oxygen.

A particularly preferred class of compounds is of the formula (II).

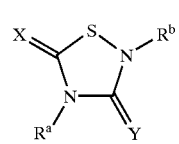

(II)

where $R^a$ and $R^b$ are independently selected from hydrogen, alkyl, cycloalkyl, haloalkyl, aryl, —(Z)$_n$-aryl, heteroaryl, —O$R^3$, —C(O)$R^3$, —C(O)O$R^3$, —(Z)$_n$—C(O)O$R^3$ and —S(O)$_t$—, and Z, n, t, $R^3$, $R^4$, X and Y are as defined above.

In the formula (II), X and Y are preferably selected from oxygen, sulphur, and —N$R^3$— where $R^3$ is heterocyclic, especially a 6-membered heterocycle which has one heteroatom which is nitrogen, being optionally aromatic and optionally oxidised or quaternised. More preferably, both X and Y are both oxygen.

Preferably $R^a$ and $R^b$ are independently selected from hydrogen, alkyl, cycloalkyl, aryl (optionally substituted with a group selected from alkyl, halo and alkoxy), —C($R^3$)($R^4$)-aryl (the aryl part being optionally substituted with a group selected from alkyl, halo and alkoxy), —O$R^3$, —C(O)O$R^3$ and —C($R^3$)($R^4$)—C(O)O$R^3$, and $R^3$ and $R^4$ are independently selected from hydrogen, alkyl and heterocyclic.

More preferably $R^a$ and $R^b$ are independently selected from alkyl, aryl (optionally substituted with a group selected from alkyl, halo and alkoxy), —$CH_2$-aryl (the aryl part being optionally substituted with a group selected from alkyl, halo and alkoxy), and —$CH_2$—$C(O)OR^3$ where $R^3$ is hydrogen or alkyl.

Still more preferably, $R^a$ and $R^b$ are independently selected from methyl, ethyl, propyl, benzyl, phenyl (optionally substituted with a group selected from methyl, fluoro, chloro, bromo and methoxy) and —$CH_2$—$C(O)O$-ethyl.

The most preferred compounds of formula (II) are listed in Table I below.

TABLE 1

| $R^a$ | $R^b$ | X | Y |
|---|---|---|---|
| $CH_2Ph$ | Me | O | O |
| Et | Me | O | O |
| Ph | Me | O | O |
| $CH_2CO_2Et$ | Me | O | O |
| 4-OMePh | Me | O | O |
| 4-MePh | Me | O | O |
| 4-BrPh | Me | O | O |
| 4-FPh | Me | O | O |
| 4-ClPh | Me | O | O |
| $CH_2Ph$ | $CH_2Ph$ | O | S |
| Ph | Ph | O | S |

Another preferred class of compounds of the invention are those compounds of formula (III):

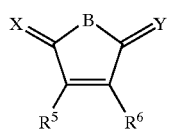

(III)

wherein:

B is —$NR^7$— or $C(R^7)(R^8)$— (wherein $R^7$ and $R^8$ are independently selected from hydrogen, alkyl, aryl, —$CH_2$—W-aryl, and —W—$CO_2H$, and W is a single bond, $CH_2$ or CO);

$R^5$ and $R^6$ are independently selected from hydrogen, alkyl, aryl and —$CH_2$-aryl; and X and Y are independently selected from =O and =S.

In the formula (III), B is preferably —$NR^7$—, wherein $R^7$ is selected from hydrogen, alkyl and —$CH_2$-aryl, especially hydrogen, methyl or benzyl.

$R^5$ and $R^6$ are preferably hydrogen.

X and Y are preferably oxygen.

The most preferred compounds of formula (III) are listed in Table 2 below.

TABLE 2

| B | X | Y | $R^5$ | $R^6$ |
|---|---|---|---|---|
| NH | O | O | H | H |
| N—$CH_2Ph$ | O | O | H | H |
| NMe | O | O | H | H |
| $CH_2$ | O | O | H | H |

Examples of further classes of compounds of formula I include those where:

a) A is —$CH_2$—; E is —$CR^1R^2$—, preferably —$CH_2$—; G is —$CR^1R^2$—, preferably —$CH_2$—;

b) A is —$CH_2$—; E is —$CR^1$—, preferably —CH—; G is —$CR^1$—, preferably —CH—; and - - - is a second bond between G and E;

c) A is —O—; E is —$CR^1$—, preferably —CH—; G is —$CR^1$—, preferably —CH—; and - - - is a second bond between G and E;

d) A is —$NR^1$—, where $R^1$ is preferably hydrogen, alkyl or aralkyl; E is —$CR^1$—, preferably —CH—; G is —$CR^1$—, preferably —CH—; and - - - is a second bond between G and E;

e) A is —$NR^1$—, where $R^1$ is preferably hydrogen or aralkyl; E is —$CR^1R^2$—, preferably —$CH_2$—; G is —$CR^1R^2$—, preferably —$CH_2$—;

f) A is —$NR^1$—, where $R^1$ is preferably hydrogen or aralkyl; E is —$CR^1$—; G is —$CR^1$—; - - - is a second bond between E and G; and E with G form a fused aryl group, preferably a phenyl group;

g) A is —$NR^1$—, where $R^1$ is preferably hydrogen, alkyl, carboxyalkyl, aroylalkyl or aralkyl; E is —S; G is —$C(R^1)_2$—, preferably —$CH_2$—;

h) A is —$NR^1$, where $R^1$ is preferably aryl; E is —$NR^1$—, where $R^1$ is preferably hydrogen or alkyl; G is —$NR^1$—, where $R^1$ is preferably hydrogen or alkyl.

In these classes of compounds, X and Y are preferably both O, though for class (g) X can be O and Y can be S. When E with G form a fused phenyl group, the resultant compounds are phthalimido derivatives.

Synthesis of the Compounds of the Invention

The compounds of the invention can be synthesised by available procedures.

For preferred compounds of formula (II) a general procedure is available [Martinez, A.; Castro, A.; Cardelús, I.; Llenas, J.; Palacios, J. M. *Bioorg. Med. Chem.*, 1997, 5, 1275–1283].

Concretely, the compounds of general formula (II) and collected in Table I, were prepared following the synthetic procedure depicted in scheme 1, and using the reactivity of N-alkyl-S-[N'-chlorocarbamoyl)amino]isothiocarbamoyl chlorides with different alkyl isocyanates. The isothiocyanates chlorination is performed by addition of an equimolecular quantity of chlorine over an hexane solution of the mentioned isothiocyanate at –15° C. The reaction of the iminochloroalkylsulfenyl chloride formed with alkyl or aryl isocyanate under inert atmosphere and subsequent hydrolysis, yielded the thiadiazolidinediones described in table I.

Scheme 1

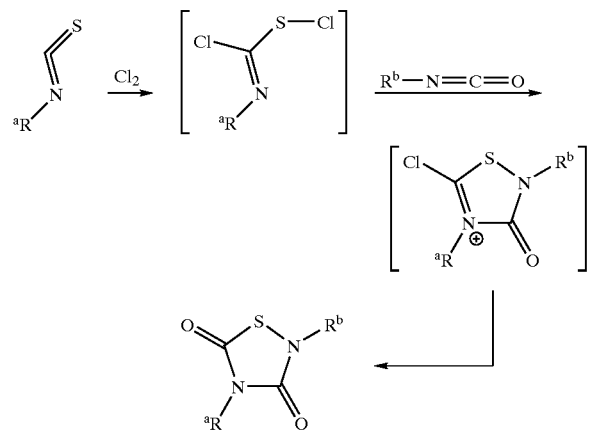

The typical compounds of this invention selectively inhibit GSK-3β without inhibition of others protein kinases such as PKA, PKC, CK-2 and CdK2, which could eliminate the widespread effects. GSK-3β is involved in the aetiopathogenesis of AD and it is responsible for the abnormal hyperphosphorylation of the tau protein. The selective inhibitors here disclosed can be useful therapeutical agents for the treatment of neurodegeneratives diseases associated to the pathology of tau protein, specially for AD which forms part of this invention. The inhibitory action of these compounds against GSK-3, leads for the design of drugs able to stop the formation of the neurofibrilar tangles, one of the hallmark present in this neurodegenerative process.

These compounds can be useful for the treatment of other pathologies in which the GSK-3β is involved, such as non-insulin-dependent diabetes mellitus.

Additionally, these compounds can be useful for the treatment of hyperproliferative diseases such as displasias and metaplasias of different tissues, psoriasis, artherioschlerosis, resthenosis and cancer, due to their inhibition of cellular cycle which forms part of this invention.

Accordingly, the present invention further provides pharmaceutical compositions comprising a compound of this invention together with a pharmaceutically acceptable carrier or diluent. Appropriate dosage forms and dosing rates can be devised and adopted in accordance with conventional practice.

EXAMPLES

Example 1

Enzymatic Inhibition of the Compounds of the Invention

GSK-3β inhibition: The GSK-3 activity was determined by incubation of a mixture of GSK-3 enzyme (Sigma), a phosphate source and a GSK-3 substrate in the presence and in the absence of the corresponding test compound, and by measuring the GSK-3 activity of this mixture.

Concretely, the GSK-3 activity is determined by incubating the enzyme at 37° C. during 20 minutes in a final volume of 12 μl of buffer (50 mM tris, pH=7.5, 1 mM EDTA, 1 mM EGTA, 1 mM DTT, 10 mM Cl$_2$Mg) supplemented with 15 μM (final concentration) of the synthetic peptide GS 1 [Woodgett, J. R. "Use of peptides for affinity purification of protein-serine kinases", Anal. Biochem., 1989, 180, 237–241] as substrate, 15 μM of ATP, 0.2 μC$_i$ of [γ-$^{32}$P]ATP and different concentrations of the test compound. The reaction is quenched by addition of an aliquot of the reaction mixture in phosphocelullose p81 papers. These papers are washed three times with phosphoric acid 1% and the radioactivity incorporated to the GS 1 peptide is measured in a liquid scintillation counter.

Compounds showed in table 1 are representative of the GSK-3 inhibitory activity object of this invention. The IC$_{50}$ (concentration at which a 50% of enzyme inhibition is shown) values are gathered in Table 3 below. The synthesis of the compounds listed in Table 3 is described below.

TABLE 3

(II)

| Compound No. | R$^a$ | R$^b$ | X | Y | IC$_{50}$ (μM) |
|---|---|---|---|---|---|
| 1 | CH$_2$Ph | Me | O | O | 1 |
| 2 | Et | Me | O | O | 5 |
| 3 | Et | nPr | O | O | 10 |
| 4 | Et | cyclohexyl | O | O | 10 |
| 5 | Ph | Me | O | O | 2 |
| 6 | CH$_2$CO$_2$Et | Me | O | O | 5 |
| 7 | 4-OMePh | Me | O | O | 5 |
| 8 | CH$_2$Ph | Et | O | O | 7 |
| 9 | Et | iPr | O | O | 35 |
| 10 | CH$_2$Ph | Et | O | S | 6 |
| 11 | CH$_2$Ph | CH$_2$Ph | O | S | 10 |
| 12 | Ph | Ph | O | S | 20 |
| 13 | Et | Et | O | S | 20 |
| 14 | Cyclohexyl | Me | O | O | >100 |
| 15 | 4-MePh | Me | O | O | 5 |
| 16 | 4-BrPh | Me | O | O | 3 |
| 17 | 4-FPh | Me | O | O | 4 |
| 18 | 4-ClPh | Me | O | O | 4 |
| 19 | Et | Me |  | O | >100 |
| 20 | Et | Et |  | O | >100 |
| 21 | Et | H |  | O | >100 |
| 22 | Me | Me |  | O | >100 |
| 23 | Et | Me |  | O | >100 |
| 24 | Et | Me |  | O | >100 |
| 25 | Et | Me |  | O | >100 |
| 26 | Et | Me |  | S | 10 |

Methods for the Synthesis of the Compounds Depicted in Table 3
General Method for the Synthesis of 1,2,4-thiadiazolidin-3,5-diones (Compounds 1–18)

Chlorine (generated by the addition of 35% HCl to $KMnO_4$) was bubbled slowly through a solution of aryl or alkyl isothiocyanate in dry hexane (25 ml), under a nitrogen atmosphere, at −15° C. to −10° C. The temperature of the reaction mixture was carefully controlled during the addition step. At this point, the N-aryl or N-alkyl-S-chloroisothiocarbamoyl chloride (see Scheme 1 above) was formed. Afterwards, alkyl isocyanate was added, and the mixture was stirred at room temperature for between 8 and 10 h. After this time, the resulting product was purified by suction filtration and recrystallization or silica gel column chromatography using the appropriate eluant. Sometimes, the 5-oxo-1,2,4-thiadiazolidine-3-thione was isolated as a by-product.

Specific Methods and Data for the Compounds Listed in Table 3

4-Benzyl-2-methyl-1,2,4-thiadiazolidine-3,5-dione (compound 1) and 2,4-Dibenzyl-5-oxo-thiadiazolidine-3-thione (compound 11)

Reagents: Benzyl iso-thiocyanate (0.86 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation (1): filtration of reaction mixture.
Purification: recrystallization from hexane.
  Yield: 0.75 g (35%) as white solid; mp 60–61° C. $^1$H-NMR ($CDCl_3$): 3.2 (s, 3H, $CH_3$); 4.8 (s, 2H, $CH_2$-Bn); 7.31–7.45 (m, 5H, arom.). $^{13}$C-NMR ($CDCl_3$): 31.4 ($CH_3$); 46.0 ($CH_2$-Bn) 128.2; 128.6; 128.8; 135.1 (C arom.); 155.2 (3-C=O); 165.6 (5-C=O). Anal. ($C_{10}H_{10}N_2SO_2$) C, H, N, S.
Isolation (11): The filtrate was evaporated.
Purification: silica gel column chromatography using $CH_2Cl_2$/Hexane (1:1).
  Yield: 0.08 g (8%) as yellow solid; mp 91–95° C. $^1$H-NMR ($CDCl_3$): 4.52 (s, 2H, $CH_2$-Bn); 5.10 (s, 2H, $CH_2$-Bn); 7.31–7.52 (m, 10H, arom.). $^{13}$C-NMR ($CDCl_3$): 50.1 ($CH_2$-Bn); 54.3 ($CH_2$-Bn); 128.1; 128.4; 128.9; 135.4 (C arom.); 127.1; 127.4; 128.4; 138.6 ('C arom.); 148.1 (3-C=S); 169.0 (5-C=O). Anal. ($C_{16}H_{14}N_2S_2O$) C, H, N, S.

4-Ethyl-2-methyl-1,2,4-thiadiazolidine-3,5-dione (compound 2)

Synthesis of this compound is described in Martinez, A.; Alonso, D.; Castro, A.; Arán, J. V.; Cardelus, I.; Baños, J. E.; Badía, A., Arch. Pharm. Pharm. Med. Chem., 1999, 332, 191–194, the contents of which are incorporated herein by reference thereto.

4-Ethyl-2-n-propyl-1,2,4-thiadiazolidine-3,5-dione (compound 3)

Synthesis of this compound is described in Martinez, A.; Alonso, D.; Castro, A.; Arán, J. V.; Cardelus, I.; Baños, J. E.; Badía, A., Arch. Pharm. Pharm. Med. Chem., 1999, 332, 191–194; the contents of which are incorporated herein by reference thereto.

2-Cyclohexyl-4-ethyl-1,2,4-thiadiazolidine-3,5-dione (compound 4) and 2,4-diethyl-5-oxo-1,2,4-thiadiazolidine-3,5-dione (compound 13)

Reagents: Ethyl isothiocyanate (0.56 ml, 6.5 mmol), 35% HCl (3.1 ml), $KMnO_4$ (0.5 g), cyclohexyl isocyanate (0.825 ml, 6.5 mmol).
Conditions: Room Temperature, 10 h.
Purification: silica gel column chromatography using AcOEt/Hexane (1:10).

Yield: The first fraction 0.12 g of compound 4 (2%) as yellow oil. $^1$H-NMR ($CDCl_3$): 1.20 (t, 3H, $CH_2CH_3$, J=7.1 Hz); 1.31 (t, 3H, $CH_2$'$CH_3$, J=7.2 Hz); 3.33 (c, 2H, '$CH_2CH_3$, J=7.2 Hz); 3.89 (c, 2H, $CH_2CH_3$, J=7.1 Hz). $^{13}$C-NMR ($CDCl_3$): 12.2 ($CH_2CH_3$); 15.7 ($CH_2$'$CH_3$); 42.4 ($CH_2CH_3$); 45.8 ('$CH_2CH_3$); 146.3 (3-C=S); 168.2 (5-C=O). Anal. ($C_6H_{10}N_2OS_2$) C, H, N, S.

The second fraction 0.73 mg of compound 13 as white solid (49%); mp=45–48° C.
  $^1$H-NMR ($CDCl_3$): 1.20 (t, 3H, $CH_2CH_3$, J=7.1 Hz); 1.31–1.92 (m, 5H, chex); 3.72 (c, 2H, $CH_2CH_3$, J=7.1 Hz). $^{13}$C-NMR ($CDCl_3$): 13.0 ($CH_2CH_3$); 39.8 ($CH_2CH_3$); 24.7; 25.1; 31.73; 53.71(C chex); 152.2 (3-C=O); 166.2 (5-C=O); Anal. ($C_{10}H_{16}N_2O_2S$) C, H, N, S.

4-Phenyl-2-methyl-1,2,4-thiadiazolidin-3,5-dione (compound 5) and 2,4-diphenyl-5-oxo-thiadiazolidine-3-thione (compound 12)

Reagents: Phenyl isothiocyanate (0.78 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation (5): filtration of reaction mixture.
Purification: recrystallization from methanol.
  Yield: 0.25 g (30%) as white solid; mp 174–179° C. $^1$H-NMR ($CDCl_3$): 3.21 (s, 3H, $CH_3$); 7.31–7.50 (m, 5H, arom.). $^{13}$C-NMR ($CDCl_3$): 31.7 ($CH_3$); 127.2; 129.2; 129.4; 132.7 (C arom.); 152.7 (3-C=O); 165.3 (5-C=O). Anal. ($C_8H_8N_2SO_2$) C, H, N, S.
Isolation (12): The filtrate was evaporated
Purification: silica gel column chromatography using $CH_2Cl_2$.
  Yield: 0.14 g (15%) as yellow solid; mp 105–110° C. $^1$H-NMR ($CDCl_3$): 6.70–7.01 (m, 5H, arom); 7.12–7.33 (m, 5H, 'arom.). $^{13}$C-NMR ($CDCl_3$): 127.2; 128.6; 129.4; 132.7 (C arom.); 128.7; 129.2; 129.7; 146.7 ('C arom.); 152.4 (3-C=S); 169.3 (5-C=O). Anal. ($C_{14}H_{10}N_2S_2O$) C, H, N, S.

The synthesis of compound 5 by a different synthetic route is described in Slomezynska, U.; Barany, G., J. Heterocyclic. Chem., 1984, 21, 241, the contents of which are incorporated herein by reference thereto.

4-(Ethoxycarbonylmethyl)-2-methyl-1,2,4-thiadiazolidine-3,5-dione (compound 6)

Reagents: Ethyl isothiocyanatoacetate (0.8 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation: filtration of reaction mixture.
Purification: recrystallization from hexane.
  Yield 0.28 g (20%) as white solid; mp 67–69° C. $^1$H-NMR ($CDCl_3$): 1.3 (t, 3H, $CH_2CO_2CH_2CH_3$, J=7.1 Hz); 3.2 (s, 3H, $CH_3$); (c, 2H, $CH_2CO_2CH_2CH_3$, J=7.1 Hz); 4.4 (s, 2H, $CH_2CO_2CH_2CH_3$). $^{13}$C-NMR ($CDCl_3$): 14.0 ($CH_2CO_2CH_2CH_3$); 31.5 ($CH_3$); 42.7 ($CH_2CO_2CH_2CH_3$); 62.1 ($CH_2CO_2CH_2CH_3$); 152.6 (3-C=O); 166.4 (5-C=O); 166.4 ($CO_2$). Anal. ($C_7H_{10}N_2SO_3$) C, H, N, S.

4-(4-Methoxyphenyl)-2-methyl-1,2,4-thiadiazolidine-3,5-dione (compound 7)

Reagents: 4-methoxyphenyl isothiocyanate (0.89 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation: filtration of reaction mixture.
Purification: recrystallization from $CH_2Cl_2$/Hexane.
  Yield: 0.44 g (30%) as white solid; mp 140–144° C. $^1$H-NMR ($CDCl_3$): 3.31 (s, 3H, $CH_3$); 3.80 (s, 3H, p-$CH_3O$-Ph); 7.02–7.32 (m, 4H, arom.). $^{13}$C-NMR ($CDCl_3$): 31.7

(CH$_3$); 55.5 (p-CH$_3$O-Ph); 114.7; 125.3; 128.5; 159.9 (C arom.); 152.9 (3-C=O); 165.5 (5-C=O). Anal. (C$_{10}$H$_{10}$N$_2$SO$_3$) C, H, N, S.

4-Benzyl-2-ethyl-1,2,4-thiadiazolidine-3,5-dione (compound 8)

Reagents: Benzyl isothiocyanate (0.86 ml, 6.5 mmol), 35% HCl (3.1 ml), KMnO$_4$ (0.5 g), ethyl isocyanate (0.51 ml, 6.5 mmol).

Conditions: Room temperature, 10 h. Purification: silica gel column chromatography using CH$_2$Cl$_2$/Hexane (1:1) and CCTLC using CH$_2$Cl$_2$.

Yield: 0.39 g (25%) as yellow oil. $^1$H-NMR (CDCl$_3$): 1.22 (t, 3H, CH$_2$'CH$_3$, J=7.2 Hz); 3.7 (c, 2H, 'CH$_2$CH$_3$, J=7.2 Hz); 4.8 (s, 2H, CH$_2$-Bn); 7.32–7.44 (m, 5H, arom.). $^{13}$C-NMR (CDCl$_3$): 13.7 (CH$_2$'CH$_3$); 39.9 ('CH$_2$CH$_3$); 45.8 (CH$_2$-Bn); 128.1; 128.6; 128.8; 135.1 (C arom.); 152.6 (3-C=O); 165.9 (5-C=O). Anal. (C$_{11}$H$_{12}$N$_2$SO$_2$) C, H, N, S.

4-Ethyl-2-isopropyl-1,2,4-thiadiazolidin-3,5-dione (compound 9)

Synthesis of this compound is described in: Martinez, A.; Castro, A.; Cardelús, I.; Llenas, J.; Palacios, J. M., *Bioorg. Med. Chem.*, 1997, 5, 1275–1283, the contents of which are incorporated herein by reference thereto.

4-Benzyl-2-ethyl-5-oxo-1,2,4-thiadiazolidine-3-thione (compound 10)

Reagents: Benzyl isothiocyanate (0.86 ml, 6.5 mmol), 35% HCl (3.1 ml), KMnO$_4$ (0.5 g), ethyl isocyanate (0.57 ml, 6.5 mmol).

Conditions: Room temperature, 12 h.

Isolation: solvent evaporation.

Purification: silica gel column chromatography using CH$_2$Cl$_2$/Hexane (1:2) first and preparative thin layer chromatography using CH$_2$Cl$_2$/Hexane (1:10) after.

Yield: 0.04 g (3%) as yellow oil. $^1$H-NMR (CDCl$_3$): 1.2 (t, 3H, CH$_2$CH$_3$, J=7.0 Hz); 4.25 (c, 2H, CH$_2$CH$_3$, J=7.0 Hz); 4.5 (s, 2H, CH$_2$-Bn); 7.11–7.31 (m, 5H, arom.). $^{13}$C-NMR (CDCl$_3$): 11.2 (CH$_2$CH$_3$); 46.1 (CH$_2$-Bn); 56.2 (CH$_2$CH$_3$); 127.2; 127.3; 128.6 138.3 (C arom.); 154.3 (3-C=S); 168.7 (5-C=O). Anal. (C$_{11}$H$_{12}$N$_2$S$_2$O) C, H, N, S.

4-(4-Methylphenyl)-2-methyl-1,2,4-thiadiazolidine-3,5-dione (compound 15)

Reagents: 4-Methylphenyl isothiocyanate (0.88 ml, 6.5 mmol), 35% HCl (3.1 ml), KMnO$_4$ (0.5 g), methyl isocyanate (0.38 ml, 6.5 mmol).

Conditions: Room temperature, 6 h.

Isolation: filtration of reaction mixture.

Purification: recrystallization from CH$_2$Cl$_2$/Hexane.

Yield: 0.29 g (21%) as white solid; mp 182–184° C. $^1$H-NMR (CDCl$_3$): 2.4 (s, 3H, p-CH$_3$-Ph); 3.25 (s, 3H, CH$_3$); 7.20–7.34 (m, 4H, arom.). $^{13}$C-NMR (CDCl$_3$): 21.1 (p-CH$_3$-Ph); 31.7 (CH$_3$); 126.7; 130.0; 130.3; 139.3 (C arom.); 152.9 (3-C=O); 165.3 (5-C=O). Anal. (C$_{10}$H$_{10}$N$_2$SO$_2$) C, H, N, S.

4-(4-Bromophenyl)-2-methyl-1,2,4-thiadiazolidine-3,5-dione (compound 16)

Reagents: 4-Bromophenyl isothiocyanate (1.4 g, 6.5 mmol), 35% HCl (3.1 ml), KMnO$_4$ (0.5 g), methyl isocyanate (0.38 ml, 6.5 mmol).

Conditions: Room temperature, 9 h.

Isolation: filtration of reaction mixture.

Purification: recrystallization from hexane/CH$_2$Cl$_2$.

Yield: 0.32 g (20%) as white solid; mp 182–184° C. $^1$H-NMR (CDCl$_3$): 3.25 (s, 3H, CH$_3$); 7.25–7.61 (2 d, 4H, arom., J=8.6 Hz). $^{13}$C-NMR (CDCl$_3$): 31.6 (CH$_3$); 123.0; 128.6; 131.6; 132.5 (C arom.); 153.4 (3-C=O); 165.7 (5-C=O). Anal. (C$_9$H$_7$N$_2$SO$_2$Br) C, H, N, S.

4-(4-Fluorophenyl)-2-methyl-1,2,4-thiadiazolidine-3,5-dione (compound 17)

Reagents: 4-Fluorophenyl isothiocyanate (1.1 g, 6.5 mmol), 35% HCl (3.1 ml), KMnO$_4$ (0.5 g), methyl isocyanate (0.38 ml, 6.5 mmol).

Conditions: Room temperature, 8 h.

Isolation: filtration of reaction mixture.

Purification: recrystallization from ethanol.

Yield: 0.37 g (25%) as white solid; mp 178–180° C. $^1$H-NMR (CDCl$_3$): 3.25 (s, 3H, CH$_3$); 7.13–7.36 (m, 4H, arom.). $^{13}$C-NMR (CDCl$_3$): 31.7 (CH$_3$); 116.3; 129.1; 160.9; 164.2 (C arom.); 152.5 (3-C=O); 165.2 (5-C=O). Anal. (C$_9$H$_7$N$_2$SO$_2$F) C, H, N, S.

4-(4-Chlorophenyl)-2-methyl-1,2,4-thiadiazolidine-3,5-dione (compound 18)

Reagents: 4-Chlorophenyl isothiocyanate (1.1 g, 6.5 mmol), 35% HCl (3.1 ml), KMnO$_4$ (0.5 g), methyl isocyanate (0.38 ml, 6.5 mmol).

Conditions: Room temperature, 6 h.

Isolation: filtration of reaction mixture.

Purification: recrystallization from ethanol.

Yield: 0.47 g (30%) as white solid; mp 175–178° C. $^1$H-NMR (CDCl$_3$): 3.25 (s, 3H, CH$_3$); 7.32–7.44 (2 d, 4H, arom., J=8.9 Hz). $^{13}$C-NMR (CDCl$_3$): 31.7 (CH$_3$); 128.4; 129.6; 131.2; 135.1 (C arom.); 152.3 (3-C=O); 165.0 (5-C=O). Anal. (C$_9$H$_7$N$_2$SO$_2$Cl) C, H, N, S.

Synthesis of 5-(2-pyridylimino)-1,2,4-thiadiazolidin-3-ones (compounds 19–22 and 26)

A general method for the synthesis of these compounds is described in Martinez, A.; Castro, A.; Cardelús, I.; Lienas, J.; Palacios, J. M., *Bioorg. Med. Chem.*, 1997, 5, 1275–1283, the contents of which are incorporated herein by reference thereto.

3-(4-Ethyl-3-oxo-2-methyl-1,2,4-thiadiazolidin-5-ylidine) aminopyridine-1-oxide (compound 23)

A general method for the synthesis of this compound is described in Martinez, A.; Alonso, D.; Castro, A.; Arán, J. V.; Cardelus, I.; Baños, J. E.; Badía, A., *Arch. Pharm. Pharm. Med. Chem.*, 1999, 332, 191–194, the contents of which are incorporated herein by reference thereto.

3-[5-(4-Ethyl-2-methyl-3-oxo)imino-1,2,4-thiadiazolidyl]-1-methyl-pyridinium iodide (compound 24)

A general method for the synthesis of this compound is described in Martinez, A.; Alonso, D.; Castro, A.; Gutierrez-Puebla, E.; Baños, J. E.; Badia, A., *Eur. J. Org. Chem.*, 2000, 675–680., the contents of which are incorporated herein by reference thereto.

4-Ethyl-5-[imino-(1-methyl-piperidin-3-yl)]-2-methyl-1,2,4-thiadiazolidin-3-one (compound 25)

A general method for the synthesis of this compound is described in Martinez, A.; Alonso, D.; Castro, A.; Gutierrez-Puebla, E.; Baños, J. E.; Badia, A., *Eur. J. Org. Chem.*, 2000, 675–680, the contents of which are incorporated herein by reference thereto.

Further compounds of formula (II) have been synthesised and their GSK-3 inhibition tested. These compounds are listed in Table 3a below.

TABLE 3a (II)

$$X \diagup\!\!\!\!\diagdown \stackrel{S}{\phantom{X}} \diagdown\!\!\!\!\diagup Rb$$

(structure of 1,2,4-thiadiazolidine with substituents Ra, Rb, X, Y)

| Compound No. | R$^a$ | R$^b$ | X | Y | IC$_{50}$ (μM) | Ref. |
|---|---|---|---|---|---|---|
| 27 | Et | Et | O | O | 25 | JMC, JHC |
| 28 | Et | Et | O | S | 20 | JMC |
| 29 | Bn | Bn | O | O | 10 | JMC, JHC |
| 30 | CH$_2$CO$_2$Et | Et | O | O | 10 | below |
| 31 | CH$_2$Ph | COPh | O | O | 3 | below |
| 32 | Ph | Et | O | NH | 65 | JMC |
| 33 | CH$_2$Ph | CH$_2$CO$_2$Et | O | O | 4 | below |
| 34 | 4-CF$_3$Ph | Me | O | O | 6 | JMC |
| 35 | n-Bu | Et | O | O | 70 | JMC |
| 36 | CH$_2$Ph | Et | O | N—OH | 6 | below |
| 37 | 3-BrPh | Me | O | O | 4 | JMC |
| 38 | 2-BrPh | Me | O | O | 6 | JMC |
| 39 | Ph | Et | O | NCONHEt | 75 | JMC |
| 40 | Ph | CO$_2$Et | S | NCO$_2$Et | >10 | JMC |
| 41 | CH$_2$CH$_2$Ph | Et | O | O | 8 | below |
| 42 | CH$_2$Ph | H | O | O | 50 | below |
| 43 | Ph | Et | O | O | 6 | ACIE |
| 44 | CH$_2$CO$_2$Et | CH$_2$CO$_2$Et | O | O | 4 | below |
| 45 | CH$_2$CO$_2$Et | Me | O | O | 2 | below |
| 46 | CH$_2$CO$_2$Et | iPr | O | O | 7 | below |
| 47 | CH$_2$CO$_2$Et | Bz | O | O | 4 | below |
| 48 | Naphthyl | Me | O | O | 3 | JMC |
| 49 | 4-NO$_2$—Ph | Et | O | O | 8.5 | below |
| 50 | Ph | Et | O | N—OH | 100 | below |
| 51 | CH$_2$Ph | iPr | O | O | 10 | below |
| 52 | Ph | Ph | O | O | 8 | ACIE |
| 53 | 4-MeOPh | Et | O | O |  | below |
| 54 | 4-MePh | Et | O | O |  | below |
| 55 | 4-BrPh | Et | O | O |  | below |

The synthesis of the known compounds depicted in Table 3a is described in the following publications, the contents of which are incorporated herein by reference thereto:
JMC: Martinez, A; Alonso, M.; Castro, A.; Perez, C.; Moreno, F. J. *J. Med. Chem.* (2002) 45:1292–1299.
JCH: *J. Heterocyclic Chem.* (1984) 21:241.
ACIE: *Angew Chem. Int. Ed.* (1966) 5:672.

The synthesis of the new compounds depicted in Table 3a is described below.

4-(Ethoxycarbonylmethyl)-2-ethyl-1,2,4-thiadiazolidine-3,5-dione (compound 30)
Reagents: Ethyl isothiocyanatoacetate (0.8 ml, 6.5 mmol), 35% HCl (3.1 ml), KMnO$_4$ (0.5 g), ehtyl isocyanate (0.51 ml, 6.5 mmol).
Conditions: Room temperature, 8 h.
Isolation: filtration of reaction mixture.
Purification: recrystallization from hexane.
Yield 0.52 g (34%) as white solid; mp 62–63° C. $^1$H-NMR (CDCl$_3$): 1.3 (t, 3H, CH$_2$CO$_2$CH$_2$CH$_3$, J=7.1 Hz); 1.3 (t, 3H, CH$_2$CH$_3$, J=7.1 Hz); 3.7 (c, 2H, CH$_2$CH$_3$, J=7.1 Hz); 4.2 (c, 2H, CH$_2$CO$_2$CH$_2$CH$_3$, J=7.1 Hz); 4.4 (s, 2H, CH$_2$CO$_2$CH$_2$CH$_3$). $^{13}$C-NMR (CDCl$_3$): 13.7 (CH$_2$CH$_3$); 14.0 (CH$_2$CO$_2$CH$_2$CH$_3$); 40.1 (CH$_2$CH$_3$); 42.6 (CH$_2$CO$_2$CH$_2$CH$_3$); 62.1 (CH$_2$CO$_2$CH$_2$CH$_3$); 152.0 (3-C=O); 165.7 (5-C=O); 166.4 (CO$_2$). Anal. (C$_8$H$_{12}$N$_2$SO$_3$) C, H, N, S.

2-Benzoyl-4-benzyl-1,2,4-thiadiazolidine-3,5-dione (compound 31)
Reagents: Benzyl isothiocyanate (0.86 ml, 6.5 mmol), 35% HCl (3.1 ml), KMnO$_4$ (0.5 g), benzoyl isocyanate (0.81 ml, 6.5 mmol).
Conditions: Room temperature, 9 h.
Isolation: solvent evaporation.
Purification: silica gel column chromatography using AcOEt/Hexane (1:10).
Yield: 0.2 g (10%) as white solid. $^1$H-NMR (CDCl$_3$): 4.8 (s, 2H, CH$_2$-Ph); 7.3–7.7 (m, 10H, arom.). $^{13}$C-NMR (CDCl$_3$): 45.9 (CH$_2$-Ph); 127.9; 128.5; 128.8; 129.0; 129.2; 132.9; 134.3 (C arom); 149.0 (3-C=O); 164.7 (COPh); 166.5 (5-C=O). Anal. (C$_{16}$H$_{12}$N$_2$SO$_3$) C, H, N, S.

4-Benzyl-2-(Ethoxycarbonylmethyl)-1,2,4-thiadiazolidine-3,5-dione (compound 33)
Reagents: Benzyl isothiocyanate (0.86 ml, 6.5 mmol), 35% HCl (3.1 ml), KMnO$_4$ (0.5 g), Ethyl isocyanatoacetate (0.73 ml, 6.5 mmol).
Conditions: Room temperature, 9 h.
Isolation: solvent evaporation.
Purification: silica gel column chromatography using AcOEt/Hexane (1:6).
Yield: 0.75 g (39%) as colorless oil. $^1$H-NMR (CDCl$_3$): 1.25 (t, 3H, CH$_2$CO$_2$CH$_2$CH$_3$, J=7.1 Hz); 4.21 (c, 2H, CH$_2$CO$_2$CH$_2$CH$_3$, J=7.1 Hz); 4.30 (s, 2H, CH$_2$CO$_2$CH$_2$CH$_3$); 4.8 (s, CH$_2$-Ph); 7.3–7.5 (m, 5H, arom.). $^{13}$C-NMR (CDCl$_3$): 13.7 (CH$_2$CO$_2$CH$_2$CH$_3$); 45.3 (CH$_2$CO$_2$CH$_2$CH$_3$); 45.7 (CH$_2$-Ph); 127.3; 128.3; 128.4; 134.7 (C arom.); 153.3 (3-C=O); 165.7 (5-C=O); 166.8 (CH$_2$CO$_2$CH$_2$CH$_3$). Anal. (C$_{13}$H$_{14}$N$_2$SO$_4$) C, H, N, S.

4-Benzyl-2-ethyl-1,2,4-thiadiazolidine-3-one-5-oxime (compound 36)
Reagents: 5-chloro-4-benzyl-2-ethyl-3-oxo-1,2,4-thiadiazolium chloride (1.24 g, 4.5 mmol), hydroxylamine hydrochloride (0.35 g, 5 mmol), pyridine (0.8 ml, 10 mmol).
Conditions: Room temperature, 12 h.
Isolation: solvent evaporation.
Purification: silica gel column chromatography using AcOEt/Hexane (1:6).
Yield: 0.10 g (9%) as yellow oil. $^1$H-NMR (CDCl$_3$): 1.22 (t, 3H, CH$_2$CH$_3$, J=7.1 Hz); 3.60 (c, 2H, CH$_2$CH$_3$, J=7.1 Hz); 4.78 (s, 2H, CH$_2$Ph); 6.57 (s, 1H, N—OH); 7.24–7.40 (m, 5H, arom). $^{13}$C-NMR (CDCl$_3$): 13.5 (CH$_2$CH$_3$); 40.2 (CH$_2$CH$_3$); 46.9 (CH$_2$Ph); 127.8; 128.4; 128.5; 135.2 (C arom.); 152.2 (3-C=O); 154.6 (5-C=NOH). Anal. (C$_{11}$H$_{13}$N$_3$SO$_2$) C, H, N, S.

2-Ethyl-4-phenethyl-1,2,4-thiadiazolidine-3,5-dione (compound 41)
Reagents: phenethyl isothiocyanate (0.97 ml, 6.5 mmol), 35% HCl (3.1 ml), KMnO$_4$ (0.5 g), ethyl isocyanate (0.51 ml, 6.5 mmol).
Conditions: Room temperature, 10 h.
Isolation: solvent evaporation.
Purification: silica gel column chromatography using AcOEt/Hexane (1:6).
Yield: 0.26 g (16%) as yellow oil. $^1$H-NMR (CDCl$_3$): 1.22 (t, 3H, CH$_2$CH$_3$, J=7.1 Hz); 2.95 (m, 2H, CH$_2$CH$_2$Ph); 3.63 (c, 2H, CH$_2$CH$_3$, J=7.1 Hz); 3.89 (m, 2H, CH$_2$CH$_2$Ph); 7.20–7.29 (m, 5H, arom). $^{13}$C-NMR (CDCl$_3$): 13.6 (CH$_2$CH$_3$); 33.6 (CH$_2$CH$_2$Ph); 39.9 (CH$_2$CH$_2$Ph); 43.5 (CH$_2$CH$_3$); 126.6; 128.5; 128.8; 137.3 (C arom.); 152.7 (3-C=O); 165.7 (5-C=O). Anal. (C$_{12}$H$_{14}$N$_2$SO$_2$) C, H, N, S.

4-Benzyl-1,2,4-thiadiazolidine-3,5-dione (compound 42)
Reagents: Benzyl isothiocyanate (0.81 ml, 6.5 mmol), 35% HCl (3.1 ml), KMnO$_4$ (0.5 g), ethyl isocyanatoformate (0.69 ml, 6.5 mmol).
Conditions: Room temperature, 8 h.
Isolation: Deprotection in situ of the nitrogen with acid conditions.

Purification: preparative centrifugal circular thin layer chromatography (CCTLC) using CH$_2$Cl$_2$.

Yield: 0.01 g (1%) as colourless oil. $^1$H-NMR (CDCl$_3$): 4.4 (s, 2H, CH$_2$Ph); 6.1 (br, NH); 7.1–7.3 (m, 5H, arom.). $^{13}$C-NMR (CDCl$_3$): 51.1 (CH$_2$Ph); 127.1; 128.3; 129.2; 139.6 (C arom.); 152.1 (3-C=O); 165.6 (5-C=O). Anal. (C$_9$H$_8$N$_2$SO$_2$) C, H, N, S.

4-(Ethoxycarbonylmethyl)-2-(ethoxycarbonylmethyl)-1,2,4-thiadiazolidine-3,5-dione (compound 44)

Reagents: Ethyl isothiocyanatoacetate (0.8 ml, 6.5 mmol), 35% HCl (3.1 ml), KMnO$_4$ (0.5 g), ethyl isocyanatoacetate (0.73 ml, 6.5 mmol).
Conditions: Room temperature, 9 h.
Isolation: solvent evaporation.
Purification: silica gel column chromatography using AcOEt/Hexane (1:3).

Yield: 0.90 g (48%) as white solid; mp. 72–74° C. $^1$H-NMR (CDCl$_3$): 1.25 (t, 3H, 'CH$_2$CO$_2$CH$_2$CH$_3$, J=7.1 Hz); 1.26 (t, 3H, CH$_2$CO$_2$CH$_2$CH$_3$, J=7.1 Hz); 4.18 (c, 2H, 'CH$_2$CO$_2$CH$_2$CH$_3$, J=7.1Hz); 4.20 (c, 2H, CH$_2$CO$_2$CH$_2$CH$_3$, J=7.1); 4.3 (s, 2H, 'CH$_2$CO$_2$CH$_2$CH$_3$); 4.4 (s, 2H, CH$_2$CO$_2$CH$_2$CH$_3$). $^{13}$C-NMR (CDCl$_3$): 14.0 ('CH$_2$CO$_2$CH$_2$CH$_3$); 14.0 (CH$_2$CO$_2$CH$_2$CH$_3$); 42.7 (CH$_2$CO$_2$CH$_2$CH$_3$); 45.6 ('CH$_2$CO$_2$CH$_2$CH$_3$); 62.1 ('CH$_2$CO$_2$CH$_2$CH$_3$); 62.1 (CH$_2$CO$_2$CH$_2$CH$_3$); 153.0 (3-C=O); 165.7 (5-C=O); 166.1 (CH$_2$CO$_2$CH$_2$CH$_3$); 166.8 ('CH$_2$CO$_2$CH$_2$CH$_3$). Anal. (C$_{10}$H$_{14}$N$_2$SO$_6$) C, H, N, S.

4-(Ethoxycarbonylmethyl)-2-methyl-1,2,4-thiadiazolidine-3,5-dione (compound 45)

Reagents: Ethyl isothiocyanatoacetate (0.8 ml, 6.5 mmol), 35% HCl (3.1 ml), KMnO$_4$ (0.5 g), methyl isocyanate (0.38 ml, 6.5 mmol).
Conditions: Room temperature, 8 h.
Isolation: filtration of reaction mixture.
Purification: recrystallization from hexane.

Yield 0.28 g (20%) as white solid; mp 67–69° C. $^1$H-NMR (CDCl$_3$): 1.3 (t, 3H, CH$_2$CO$_2$CH$_2$CH$_3$, J=7.1 Hz); 3.2 (s, 3H, CH$_3$); 4.2 (c, 2H, CH$_2$CO$_2$CH$_2$CH$_3$, J=7.1 Hz); 4.4 (s, 2H, CH$_2$CO$_2$CH$_2$CH$_3$). $^{13}$C-NMR (CDCl$_3$): 14.0 (CH$_2$CO$_2$CH$_2$CH$_3$); 31.5 (CH$_3$); 42.7 (CH$_2$CO$_2$CH$_2$CH$_3$); 62.1 (CH$_2$CO$_2$CH$_2$CH$_3$); 152.6 (3-C=O); 166.4 (5-C=O); 166.4 (CO$_2$). Anal. (C$_7$H$_{10}$N$_2$SO$_3$) C, H, N, S.

4-(Ethoxycarbonylmethyl)-2-isopropyl-1,2,4-thiadiazolidine-3,5-dione (compound 46)

Reagents: Ethyl isothiocyanatoacetate (0.8 ml, 6.5 mmol), 35% HCl (3.1 ml), KMnO$_4$ (0.5 g), isopropyl isocyanate (0.64 ml, 6.5 mmol).
Conditions: Room temperature, 9 h.
Isolation: filtration of reaction mixture.
Purification: recrystallization from hexane.

Yield: 0.48 g (30%) as white solid; mp 80–82° C. $^1$H-NMR (CDCl$_3$): 1.3 (t, 3H, CH$_2$CO$_2$CH$_2$CH$_3$, J=7.1 Hz); 1.3 (d, 6H, CH(CH$_3$)$_2$, J=7.1 Hz); 3.8 (sp, 1H, CH(CH$_3$)$_2$, J=7.1 Hz); 4.1 (c, 2H, CH$_2$CO$_2$CH$_2$CH$_3$, J=7.1 Hz); 4.4 (s, 2H, CH$_2$CO$_2$CH$_2$CH$_3$). $^{13}$C-NMR (CDCl$_3$): 13.6 (CH$_2$CO$_2$CH$_2$CH$_3$); 20.1(CHCH$_3$CH$_3$); 45.1 (CHCH$_3$CH$_3$); 48.2 (CH$_2$CO$_2$CH$_2$CH$_3$); 59.2 (CH$_2$CO$_2$CH$_2$CH$_3$); 153.0 (3-C=O); 165.6 (5-C=O); 167.3 (CO$_2$). Anal. (C$_9$H$_{14}$N$_2$SO$_4$) C, H, N, S.

2-Benzoyl-4-(ethoxycarbonylmethyl)-1,2,4-thiadiazolidine-3,5-dione (compound 47)

Reagents: Ethyl isothiocyanatoacetate (0.8 ml, 6.5 mmol), 35% HCl (3.1 ml), KMnO$_4$ (0.5 g), benzoyl isocyanate (0.81 ml, 6.5 mmol).
Conditions: Room temperature, 9 h.
Isolation: solvent evaporation.

Purification: silica gel column chromatography using AcOEt/Hexane (1:5).

Yield: 0.07 g (4%) as colorless oil. $^1$H-NMR (CDCl$_3$): 1.26 (t, 3H, CH$_2$CO$_2$CH$_2$CH$_3$, J=7.1 Hz); 4.2 (c, 2H, CH$_2$CO$_2$CH$_2$CH$_3$, J=7.1 Hz); 4.4 (s, 2H, CH$_2$CO$_2$CH$_2$CH$_3$); 7.4–7.7 (m, 5H, arom). $^{13}$C-NMR (CDCl$_3$): 13.9 (CH$_2$CO$_2$CH$_2$CH$_3$); 42.3 (CH$_2$CO$_2$CH$_2$CH$_3$); 62.4 (CH$_2$CO$_2$CH$_2$CH$_3$); 127.9; 129.2; 131.7; 133.1 (C arom); 148.6 (3-C=O); 164.4 (5-C=O); 166.4 (CH$_2$CO$_2$CH$_2$CH$_3$); 165.7(CO-Ph). Anal. (C$_{13}$H$_{12}$N$_2$SO$_5$) C, H, N, S.

2-Ethyl-4-(4-nitrophenyl)-1,2,4-thiadiazolidine-3,5-dione (compound 49)

Reagents: 4-nitrophenyl isothiocyanate (1.17 g, 6.5 mmol), 35% HCl (3.1 ml), KMnO$_4$ (0.5 g), ethyl isocyanate (0.51 ml, 6.5 mmol) in THF.
Conditions: Room temperature, 10 h.
Isolation: solvent evaporation.
Purification: silica gel column chromatography using AcOEt/Hexane (1:4).

Yield: 0.26 g (11%) as yellow solid; mp. 117–118° C. $^1$H-NMR (CDCl$_3$): 1.34 (t, 3H, CH$_2$CH$_3$, J=7.1 Hz); 3.77 (c, 2H, CH$_2$CH$_3$, J=7.1 Hz); 7.6–8.4 (m, 5H, arom). $^{13}$C-NMR (CDCl$_3$): 13.6 (CH$_2$CH$_3$; 40.3 (CH$_2$CH$_3$); 124.3; 127.6; 137.9; 147.1 (C arom.); 150.9 (3-C=O); 164.8 (5-C=O). Anal. (C$_{10}$H$_9$N$_3$SO$_4$) C, H, N, S.

2-Ethyl-4-phenyl-1,2,4-thiadiazolidine-3-one-5-oxime (compound 50)

Reagents: 5-chloro-4-phenyl-2-ethyl-3-oxo-1,2,4-thiadiazolium chloride (1.24 g, 4.5 mmol), hydroxylamine hydrochloride (0.35 g, 5 mmol), pyridine (0.8 ml, 10 mmol).
Conditions: Room temperature, 12 h.
Isolation: solvent evaporation.
Purification: silica gel column chromatography using AcOEt/Hexane (1:4) first, and then preparative centrifugal circular thin layer chromatography (CCTLC) using AcOEt/Hexane (1:3).

Yield: 0.13 g (12%) as yellow solid; mp. 115–117° C. $^1$H-NMR (CDCl$_3$): 1.28 (t, 3H, CH$_2$CH$_3$, J=7.1 Hz); 3.64 (c, 2H, CH$_2$CH$_3$, J=7.1 Hz); 6.65 (s, 1H, N—OH); 7.24–7.50 (m, 5H, arom). $^{13}$C-NMR (CDCl$_3$): 13.4 (CH$_2$CH$_3$); 40.2 (CH$_2$CH$_3$); 127.0; 128.6; 129.2; 133.8 (C arom.); 152.4 (3-C=O); 153.5 (5-C=NOH). Anal. (C$_{10}$H$_{11}$N$_3$SO$_2$) C, H, N, S.

4-Benzyl-2-isopropyl-1,2,4-thiadiazolidine-3,5-dione (compound 51)

Reagents: Benzyl isothiocyanate (0.81 ml, 6.5 mmol), 35% HCl (3.1 ml), KMnO$_4$ (0.5 g), isopropyl isocyanate (0.64 ml, 6.5 mmol).
Conditions: Room temperature, 8 h.
Isolation: solvent evaporation.
Purification: silica gel column chromatography using AcOEt/Hexane (1:3).

Yield: 0.50 g (31%) as yellow oil. $^1$H-NMR (CDCl$_3$): 1.2 (d, 6H, CH(CH$_3$)$_2$, J=6.6 Hz); 4.7 (sp, 1H, CH(CH$_3$)$_2$, J=6.6 Hz); 4.8 (s, 2H, CH$_2$Ph); 7.2–7.4 (m, 5H, arom.). $^{13}$C-NMR (CDCl$_3$): 21.2 ((CH$_3$)$_2$CH); 45.5 (CH(CH$_3$)$_2$); 47.0 (CH$_2$Ph); 127.8; 128.4; 128.5; 135.0 (C arom.); 151.9 (3-C=O); 165.8 (5-C=O). Anal. (C$_{12}$H$_{14}$N$_2$SO$_2$) C, H, N, S.

2-Ethyl-4-(4-methoxyphenyl)-1,2,4-thiadiazolidine-3,5-dione (compound 53)

Reagents: 4-Methoxyphenyl isothiocyanate (0.89 ml, 6.5 mmol), 35% HCl (3.1 ml), KMnO$_4$ (0.5 g), ethyl isocyanate (0.51 ml, 6.5 mmol).
Conditions: Room temperature, 8 h.

Isolation: solvent evaporation.
Purification: silica gel column chromatography using AcOEt/Hexane (1:4).

Yield: 0.344 g (21%) as white solid. $^1$H-NMR (CDCl$_3$): 1.2 (t, 3H, CH$_3$CH$_2$ J=7.2 Hz); 3.6 (c, 2H, CH$_3$CH$_2$, J=7.2 Hz); 3.7 (s, 3 H, p-CH$_3$O-Ph); 6.9–7.2 (2d, 4H, arom., J=9.4 Hz). $^{13}$C-NMR (CDCl$_3$): 14.2 (CH$_3$CH$_2$); 40.6 (CH$_3$CH$_2$); 55.8 (p-CH$_3$O-Ph); 114.7; 125.6; 128.7; 159.9 (C arom.); 152.4 (3-C=O); 165.8 (5-C=O). Anal. (C$_{11}$H$_{12}$N$_2$SO$_3$) C, H, N, S.

2-Ethyl-4-(4-methylphenyl)-1,2,4-thiadiazolidine-3,5-dione (compound 54)
Reagents: 4-Methylphenyl isothiocyanate (0.88 ml, 6.5 mmol), 35% HCl (3.1 ml), KMnO$_4$ (0.5 g), ethyl isocyanate (0.51 ml, 6.5 mmol).
Conditions: Room temperature, 8 h.
Isolation: solvent evaporation.
Purification: silica gel column chromatography using AcOEt/Hexane (1:4).

Yield: 0.37 g (25%) as white solid. $^1$H-NMR (CDCl$_3$): 1.3 (t, 3H, CH$_3$CH$_2$, J=7.3 Hz); 2.4 (s, 3H, p-CH$_3$-Ph); 3.7 (c, 2H, CH$_3$CH$_2$, J=7.3 Hz); 7.20–7.34 (m, 4H, arom.). $^{13}$C-NMR (CDCl$_3$): 13.9 (CH$_3$CH$_2$); 21.3 (p-CH$_3$-Ph); 40.3 (CH$_3$CH$_2$); 126.8; 129.8; 129.9; 139.1 (C arom.); 152.0 (3-C=O); 165.4 (5-C=O). Anal. (C$_{11}$H$_{12}$N$_2$SO$_2$) C, H, N, S.

(4-Bromophenyl)-2-ethyl-1,2,4-thiadiazolidine-3,5-dione (compound 55)
Reagents: 4-Bromophenyl isothiocyanate (1.4 g, 6.5 mmol), 35% HCl (3.1 ml), KMnO$_4$ (0.5 g), ethyl isocyanate (0.51 ml, 6.5 mmol).
Conditions: Room temperature, 9 h.
Isolation: solvent evaporation.
Purification: silica gel column chromatography using AcOEt/Hexane (1:4).

Yield: 0.256 g (13%) as white solid. $^1$H-NMR (CDCl$_3$): 1.3 (t, 3H, CH$_3$CH$_2$, J=7.2 Hz); 3.7 (c, 2H, CH$_3$CH$_2$, J=7.2 Hz); 7.3–7.6 (2 d, 4H, arom., J=8.8 Hz). $^{13}$C-NMR (CDCl$_3$): 13.8 (CH$_3$CH$_2$); 40.4 (CH$_3$CH$_2$); 122.9; 128.5; 131.5; 132.3 (C arom.); 151.4 (3-C=O); 164.9 (5-C=O). Anal. (C$_{10}$H$_9$N$_2$SO$_2$Br) C, H, N, S.

GSK-3 inhibition: The experiments of inhibition were also performed at variable concentrations of ATP (up to 50 µM) and in all cases the same value of IC$_{50}$ were obtained. Thus could suggest that thiadiazolinediones do not compete with ATP in the binding to GSK-3.

The first four compounds were assayed for inhibition of other enzymes.

Protein kinase A (PKA) inhibition: The potential inhibition of this enzyme is evaluated by determining the esthatmine phosphorylation by the protein kinase A (PKA). The esthatmine was purified following the procedure described by Belmont and Mitchinson (Belmont, L. D.; Mitchinson, T. J. "Identification of a protein that interact with tubulin dimers and increases the catastrophe rate of microtubule", Cell, 1996, 84, 623–631).

Concretely, it was used purified PKA (Sigma, catalytic subunit from bovine heart (p 2645)) and 10–15 µg of substrate (esthatmine) in a 25 µl total volume of buffer solution containing 20 µM (γ-$^{32}$P)ATP. The cAMP kinase protein (100 ng/reaction) was performed in 50 µl of 25 mM hepes, pH 7.4, 20 mM MgCl$_2$, 2 mM EGTA, 2 mM dithiothreitol, 0.5 mM Na$_3$VO$_4$. After the reaction took place, a quenching buffer was added, the reaction mixture was boiled at 100° C. during 5 minutes and the phosphorylated protein was characterized by gel electrophoresys and quantified by autoradiographia.

In these conditions none of the compounds assayed showed any inhibition of PKA.

Protein kinase C (PKC) inhibition: The potential inhibition of this enzyme is evaluated by determining the phosphorylation of the peptide PANKTPPKSPGEPAK (Woodgett, J. R. "Use of peptides for affinity purification of protein-serine kinases", Anal. Biochem., 1989, 180, 237–241) by the protein kinase C (PKC) using phosphatidyl serine as stimulating agent. The method followed is the same described above for GSK-3.

Concretely, it was used PKC purified from rat brains following the method described by Walsh (Walsh, M. P.; Valentine, K. A.; Nagi, P. K.; Corruthers, C. A.; Hollenberg, M. D. Biochem. J., 1984, 224, 117–127) and 1–10 mM of substrate in a total volume of 25 µl of adecuated buffer solution containing 10 µM (γ-$^{32}$P)ATP.

In these conditions none of the compounds assayed showed any inhibition of PKC.

Casein kinase 2 (CK-2) inhibition: The phosphorylating activity of this enzyme against esthatmine has been measured using CK-2 purified from bovine brains, following the method described by Alcazar (Alcazar, A.; Marín, E.; Lopez-Fando, J.; Salina, M. "An improved purification procedure and properties of casein kinase II from brain", Neurochem. Res., 1988, 13, 829–836), with 3.6 µM of substrate in a total volume of 25 µl of an adequate buffer solution containing 20 µM (γ-$^{32}$P)ATP. The CK-2 assays were performed with esthatmine as substrate (see PKA determination) in 50 µl of 25 mM Hepes, pH 7.4, 20 mM MgCl$_2$, 2 mM EGTA, 2 mM dithiothreitol, 0.5 mM Na$_3$VO$_4$, and 100 ng of purified CK-2. After the reaction took place, it was followed the same method described for PKA.

In these conditions none of the compounds assayed showed any inhibition of CK-2.

Cyclin dependent protein kinase 2 (Cdc2) inhibition: The phosphorylating activity of this enzyme against histone H1 has been measured using Cdc2 (Calbiochem) following the method described by Kobayashi (Kobayashi, H.; Stewart, E.; Poon, R. Y.; Hunt, T. "Cyclin A and cyclin B dissociate from p34cdc2 with half-times of 4 and 15 h, respectively, regardless of the phase of the cell cycle", J. Biol. Chem., 1994, 269, 29153–29160), with 1 µg/µl of substrate in a total volume of 25 µl of the adequate buffer solution containing 20 µM (γ-$^{32}$P)ATP. The Cdc2 assays were performed with histone H1 as substrate (see PKA determination) in 50 µl of buffer pH 7.5, 50 mM Tris-HCl, 10 mM Cl$_2$Mg, 1 mM DTT, 1 mM EGTA, 100 µM ATP, 0.01% BRIJ-35. After the reaction took place, it was followed the same method described for PKA.

In these conditions none of the compounds assayed showed any inhibition of Cdc2.

Example 2

Analysis of the Neurites Growth After the Drug Treatment

Cells were maintained in a Dulbecco medium (DEMEM) with a 10% fethal bovine serum, glutamine (2 mM) and antibiotics. For the analysis of the potential GSK-3 inhibition in vivo, mice neuroblastoms N$_2$A cultures (Garcia-Perez, J.; Avila, J.; Diaz-Nido, J. "Lithium induces morphological differentiation of mouse neuroblastoma", J. Neurol. Res., 1999, 57, 261–270) were used. The test compounds were added to these cells cultures. This cell line has the particularity of expressed a certain kind of neuronal phenotype (neuritic extensions) after the addition of lithium chloride (10 mM), a known GSK-3 inhibitor. After 2–3 days of culture, it was check the effect of the tested compounds gathered in table I. It was observed that the generation of neuritic extension in the same extension than when lithium was added. That fact confirms the in vivo GSK-3 inhibition of the compounds of the invention.

Example 3

Cell Cycle Blockade

In parallel, the potential interference of these compounds with the cell cycle was studied on $N_2A$ cells. The cell culture was maintained in a Dulbecco medium (DEMEM) with a 10% fethal bovine serum, glutamine (2 mM) and antibiotics.

The first four compounds of general formula (I) gathered in Table 3 were assayed in the described conditions and shown ability to inhibit the cell cycle at an inhibitor concentration comprised between 100 nM and 1 $\mu$M. The cellular blockade was initially observed at concentrations comprised between 100–200 nM and was totally effective at 1 $\mu$M.

The tested compounds was non toxic in stationary fibroblast culture MRC-5 after 10 days of continue exposure to the inhibitors.

Example 4

GSK-3 Inhibition of Further Compounds

GSK-3 Inhibition Data

TABLE 4

| Family | Compound | | IC$_{50}$ ($\mu$M) |
|---|---|---|---|
| A | 1-A | | >100 |
| B | 1-B | | 12 |
| C | 1-C | | >100 |
| D | | R = H (1-D) | 6 |
| | | R = CH$_2$Ph (2-D) | 1 |
| | | R = Me (3-D) | 5 |
| E | | R = H; X, Y = O (1-E) | >100 |
| | | R = CH$_2$Ph; X, Y = O (2-E) | >100 |
| | | R = CH$_2$Ph; X = O; Y = H (3-E) | >100 |
| F | | R = H (1-F) | >100 |
| | | R = CH$_2$Ph (2-F) | >100 |

TABLE 4-continued

| Family | Compound | | IC$_{50}$ ($\mu$M) |
|---|---|---|---|
| G | | R = H (1-G) | >100 |
| | | R = Me (2-G) | >100 |
| | | R = CH$_2$CO$_2$H (3-G) | >100 |
| | | R = CH$_2$Ph (4-G) | 25 |
| | | R = CH$_2$CH$_2$Ph (5-G) | 35 |
| | | R = CH$_2$COPh (6-G) | 50 |
| H | | R = H (1-H) | >100 |
| | | R = Me (2-H) | >100 |

Detailed Synthesis of Some of the Compounds Depicted in Table 4 (Families A–H)
Synthesis of the Compounds of Family D
N-Benzylmaleimide (compound 2-D): described in Walker, M. A., *Tetrahedron Lett.*, 1994, 35, 665–668.
Synthesis of the Compounds of Family G
(4-oxo-2-thioxo-thiazolidin-3-yl)-acetic acid (compound 3-G): Girard, M. L.; Dreux, C., *Bull. Soc. Chim. Fr*, 1968, 3461–3468.
3-Benzyl-2-thioxo-thiazolidin-4-one (compound 4-G)
Reagents: Rhodanine (53 mg, 0.4 mmol), triethylamine (0.05 ml) and benzyl bromide (68 mg, 0.4 mmol) in 25 ml of acetone.
Conditions: Refluxed for 6 h.
Isolation: Add water and extract with ethyl acetate (3×5 ml).
Purification: preparative centrifugal circular thin layer chromatography (CCTLC) using CH$_2$Cl$_2$/Hexane (2:1).
Yield: 10 mg (10%) as yellow oil. $^1$H-NMR (CDCl$_3$): 3.9 (s, 2H); 5.2 (s, 2H, CH$_2$Ph); 7.3–7.4 (m, 5H, arom). $^{13}$C-NMR (CDCl$_3$): 35.4 (CH$_2$); 47.6 (CH$_2$Ph); 128.2; 128.6; 129.1; 134.7 (C arom); 153.8 (C=O); 173.8 (C=S). Anal. (C$_{10}$H$_9$NS$_2$O) C, H, N, S.
An alternative method for the synthesis of this compound is described in *J. Parkt. Chem.*, 1910, 81, 456, the contents of which are incorporated herein by reference thereto.
3-Phenethyl-2-thioxo-thiazolidin-4-one (compound 5-G)
Reagents: Rhodanine (133 mg, 1 mmol), triethylamine (0.14 ml) and phenethyl bromide (0.14 ml, 1 mmol) in 25 ml of acetone.
Conditions: Refluxed for 12 h.
Isolated: Add water and extract with ethyl acetate (3×10 ml).
Purification: preparative centrifugal circular thin layer chromatography (CCTLC) using CH$_2$Cl$_2$/Hexane (2:1).
Yield: 10 mg (4%) as yellow oil. $^1$H-NMR (CDCl$_3$): 2.9 (t, 2H, CH$_2$CH$_2$Ph, J=8.1), 3.9 (s, 2H); 4.2 (s, 2H, CH$_2$CH$_2$Ph, J=8.1); 7.4–7.9 (m, 5H, arom). $^{13}$C-NMR (CDCl$_3$): 32.6 (CH$_2$CH$_2$Ph); 35.3 (CH$_2$); 45.7 (CH$_2$CH$_2$Ph); 126.8; 128.6; 128.6; 137.4 (C arom); 173.5 (C=O); 200.9 (C=S). Anal. (C$_{11}$H$_{11}$NS$_2$O) C, H, N, S.
An alternative method for the synthesis of this compound is described in: Buck, Leonard, *J. Am. Chem. Soc.*, 1931, 53, 2688–2690, the contents of which are incorporated herein by reference thereto.
3-Phenacyl-2-thioxo-thiazolidin-4-one (compound 6-G)
Reagents: Rhodanine (133 mg, 1 mmol), K$_2$CO$_3$ (excess) and acetophenone bromide (199 mg, 1 mmol) in 25 ml of acetone.
Conditions: Stirred at room temperature for 3 h.
Isolation: Filtration of the carbonate and evaporation of the solvent to dryness in vacuo.

Purification: preparative centrifugal circular thin layer chromatography (CCTLC) using $CH_2Cl_2$.

Yield: 38 mg (15%) as brown oil. $^1$H-NMR ($CDCl_3$): 3.9 (s, 2H); 4.2 (s, 2H, $CH_2COPh$); 7.4–7.9 (m, 5H, arom). $^{13}$C-NMR ($CDCl_3$): 37.6 ($CH_2$); 45.3 ($CH_2COPh$); 128.6; 128,7; 133.5; 135.3 (C arom); 170.5 (C=O); 194.1 ($CH_2COPh$); 197.6 (C=S). Anal. ($C_{11}H_9NS_2O_2$) C, H, N, S.

Further compounds of formula (III) have been synthesised and their GSK-3 inhibition tested. These compounds are listed in Tables 4a and 4b below.

TABLE 4a

This lists further compounds of Family D in Table 4 above, ie those compounds of formula:

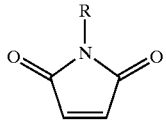

wherein R is as listed in the Table.

| Compound No. | R | GSK-3β $IC_{50}$ ($\mu M$) |
|---|---|---|
| 4-D | $(CH_2)_2Ph$ | 2 |
| 5-D | $(CH_2)_3Ph$ | 3 |
| 6-D | $(CH_2)_5Ph$ | 3 |
| 7-D | p-$OCH_3$—Bn | 2.5 |
| 8-D | p-$OCH_3$—$(CH_2)_2Ph$ | 3 |
| 9-D | $CH_2CO_2Et$ | 3 |

General Method for the Synthesis of N-alkyl-maleimides

This method is described in: Walker, M. A., *Tetrahedron Lett.*, 1995, 35, 665–668, the contents of which are incorporated herein by reference thereto.

A 50 ml round bottom flask was charged with $Ph_3P$ to which was added 25 ml of dry THF. The resulting clear solution was cooled to –70° C. under a nitrogen atmosphere. DIAD or DEAD, depending on the case, was added over 2–3 min. The yellow reaction mixture was stirred 5 min after which the corresponding alkyl alcohol was added over 1 min and stirred for 5 min. Maleimide was then added to the reaction mixture as solid. The resulting suspension was allowed to remain at –70° C. for 5 min, during which time most of the maleimide dissolved. The cooling bath was then removed, and the reaction was stirred overnight at ambient temperature. The solvent was evaporated to dryness in vacuo and the residue purified by silica gel column chromatography using as eluant mixtures of solvents in the proportions indicated for each particular case.

N-phenethylmaleimide (compound 4-D): Walker, M. A., *Tetrahedron Lett.*, 1995, 35, 665–668.

N-(3-phenylpropyl)maleimide (compound 5-D)

Reagents: $Ph_3P$ (0.65 g, 2.5 mmol), DIAD (0.5 ml, 2.5 mmol), 3-phenyl-1-propanol (0.48 ml, 3.75 mmol) and maleimide (0.24 g, 2.5 mmol).

Conditions: Room temperature, overnight.

Purification: silica gel column chromatography using AcOEt/Hexane (1:4).

Yield: 0.20 g (37%) as white solid; mp 79–80° C. $^1$H-NMR ($CDCl_3$): 1.92 (q, 2H, $CH_2CH_2CH_2Ph$, J=7.1 Hz); 2.60 (t, 2H, $CH_2CH_2CH_2Ph$, J=7.1 Hz); 3.55 (t, 2H, $CH_2CH_2CH_2Ph$, J=7.1 Hz); 6.27 (d, 2H, CH=CH, J=6.4 Hz); 7.12–7.28 (m, 5H, arom). $^{13}$C-NMR ($CDCl_3$): 29.6 ($CH_2$—$CH_2CH_2Ph$); 32.8 ($CH_2CH_2CH_2Ph$); 37.4 ($CH_2CH_2CH_2Ph$); 125.8; 128.1; 128.2; 140.7 (C arom); 133.7 (C=C); 170.6 (C=O). Anal. ($C_{13}H_{13}NO_2$) C, H, N, S.

N-(5-phenylpentyl)maleimide (compound 6-D)

Reagents: $Ph_3P$ (0.65 g, 2.5 mmol), DIAD (0.5 ml, 2.5 mmol), 5-phenyl-1-pentanol (0.63 ml, 3.75 mmol) and maleimide (0.24 g, 2.5 mmol).

Conditions: Room temperature, overnight.

Purification: silica gel column chromatography using AcOEt/Hexane (1:4).

Yield: 0.32 g (52%) as white-yellow solid; mp 49–51° C. $^1$H-NMR ($CDCl_3$): 1.20–138 (m, 2H, $CH_2CH_2CH_2CH_2$—$CH_2Ph$); 1.52–2.02 (m, 4H, $CH_2CH_2CH_2CH_2CH_2Ph$); 2.57 (t, 2H, $CH_2CH_2CH_2CH_2$—$CH_2Ph$, J=7.3 Hz); (t, 2H, $CH_2CH_2CH_2CH_2CH_2Ph$, J=7.3 Hz); 6.65 (d, 2H, CH=CH, J=6.4 Hz); 7.11–7.28 (m, 5H, arom). $^{13}$C-NMR ($CDCl_3$): 25.9 ($CH_2CH_2CH_2$—$CH_2CH_2Ph$); 28.0 ($CH_2CH_2CH_2$—$CH_2CH_2Ph$); 30.6 ($CH_2CH_2CH_2CH_2$—$CH_2Ph$); 35.4 ($CH_2CH_2CH_2CH_2$—$CH_2Ph$); 37.3 ($CH_2CH_2CH_2CH_2CH_2Ph$); 125.4; 127.9; 128.0; 142.0 (C arom); 133.6 (C=C); 170.5 (C=O) Anal. ($C_{15}H_{17}NO_2$) C, H, N, S.

N-(p-methoxybenzyl)maleimide (compound 7-D)

Reagents: $Ph_3P$ (1.31 g, 5 mmol), DEAD (0.8 ml, 5 mmol), p-methoxybenzyl alcohol (0.93 ml, 7.5 mmol) and maleimide (0.48 g, 5 mmol).

Conditions: Room temperature, overnight.

Purification: silica gel column chromatography using AcOEt/Hexane (1:3).

Yield: 0.50 g (46%) as white solid; mp. 99–102° C. $^1$H-NMR ($CDCl_3$): 3.74 (s, 3H, $OCH_3$); 4.58 (s, 2H, $CH_2Ph$); 6.65 (d, 2H, CH=CH, J=6.4 Hz); 6.8–7.2 (m, 4H, arom). $^{13}$C-NMR ($CDCl_3$): 40.4 ($CH_2Ph$-$OCH_3$); 54.8 (—$OCH_3$); 113.6; 128.2; 129.5; 158.8 (C arom); 133.8 (C=C); 170.1 (C=O) Anal. ($C_{12}H_{11}NO_3$) C, H, N, S.

N-(p-Methoxyphenethyl)maleimide (compound 8-D)

Reagents: $Ph_3P$ (1.31 g, 5 mmol), DEAD (0.8 ml, 5 mmol), p-methoxyphenethyl alcohol (1.2 g, 7.5 mmol) and maleimide (0.48 g, 5 mmol).

Conditions: Room temperature, overnight.

Purification: silica gel column chromatography using AcOEt/Hexane (1:5).

Yield: 0.71 g (60%) as yellow solid; mp. 79–81° C. $^1$H-NMR ($CDCl_3$): 2.80 (m, 2H, $CH_2CH_2Ph$); 3.70 (m, 2H, $CH_2CH_2Ph$); 3.75 (s, 3H, $OCH_3$); 6.63 (d, 2H, CH=CH, J=6.4 Hz); 6.8–7.1 (m, 4H, arom). $^{13}$C-NMR ($CDCl_3$): 33.5 ($CH_2CH_2Ph$-$OCH_3$); 39.2 ($CH_2CH_2Ph$—$OCH_3$); 55.5 (—$OCH_3$); 114.0; 129.7; 129.9; 158.4 (C arom); 133.9 (C=C); 170.5 (C=O). Anal. ($C_{13}H_{13}NO_3$) C, H, N, S.

N-(Ethoxycarbonylmethyl)maleimide (compound 9-D)

Reagents: $Ph_3P$ (1.31 g, 5 mmol), DEAD (0.8 ml, 5 mmol), ethyl glycollate (0.71 ml, 7.5 mmol) and maleimide (0.48 g, 5 mmol).

Conditions: Room temperature, overnight.

Purification: silica gel column chromatography using AcOEt/Hexane (1:3).

Yield: 0.30 g (33%) as colourless oil. $^1$H-NMR ($CDCl_3$): 1.25 (t, 3H, $CH_2CO_2CH_2CH_3$, J=7.1 Hz); 4.20 (c, 2H, $CH_2CO_2CH_2CH_3$, J=7.1 Hz); 4.24 (s, 2H, $CH_2CO_2CH_2CH_3$); 6.76 (d, 2H, CH=CH, J=6.4 Hz). $^{13}$C-NMR ($CDCl_3$): 13.7 ($CH_2CO_2CH_2CH_3$); 38.4 ($CH_2CO_2CH_2CH_3$); 61.5 ($CH_2CO_2CH_2CH_3$); 134.3 (C=C); 166.9 ($CO_2$); 169.6 (C=O). Anal. ($C_8H_9NO_4$) C, H, N, S.

TABLE 4b

This lists the activity of further compounds of Family G in Table 4 above, ie those compounds of formula:

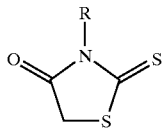

wherein R is as listed in the table.

| Compound No. | R | GSK-3β IC$_{50}$ (μM) |
|---|---|---|
| 7-G | NH$_2$ | >100 |
| 8-G | CH$_2$(4-MeO—Ph) | 65 |

GSK-3 inhibitors: For compounds belonging to family D, the GSK-3 inhibition experiments were also performed at variable concentrations of ATP (up to 50 μM) and in all cases the same value of IC$_{50}$ were obtained. Thus could suggest that these compounds do not compete with ATP in the binding to GSK-3.

Example 5

Cell Cycle Blockade

The IC$_{50}$ for some of the compounds tested in N$_2$A cell cultures are gathered in Table 5 below.

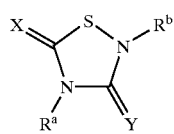
(II)

TABLE 5

| R$^a$ | R$^b$ | X | Y | IC$_{50}$ (μM) |
|---|---|---|---|---|
| CH$_2$Ph | Me | O | O | 4–8 |
| Et | Me | O | O | 40–100 |
| Et | nPr | O | O | 5–10 |
| Et | cyclohexyl | O | O | 6–9 |
| Ph | Me | O | O | 4–7 |
| CH$_2$CO$_2$Et | Me | O | O | 1–2 |
| 4-OMePh | Me | O | O | 1–2 |
| CH$_2$Ph | Et | O | O | 4–7 |
| CH$_2$Ph | CH$_2$Ph | O | O | 2–3 |
| Et | Et | O | O | 30–80 |
| CH$_2$Ph | CH$_2$Ph | O | S | 1–2 |
| Ph | Ph | O | S | 4–8 |

What is claimed is:

1. Compounds of general formula (I):

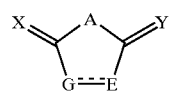
(I)

wherein:
A is —NR$^1$—;
E is —NR$^1$—;
G is —S—;
each R$^1$ is independently selected from haloalkyl, —OR$^3$, —C(O)R$^3$, —C(O)OR$^3$, —(Z)$_n$—C(O)OR$^3$ and —S(O)$_t$—;

Z is independently selected from —C(R$^3$)(R$^4$)—, —C(O)—, —O—, —C(=NR$^3$)—, —S(O)$_t$— and N(R$^3$)—;

n is zero, one, or two;

t is zero, one, or two;

R$^3$ and R$^4$ are independently selected from hydrogen, alkyl, and aryl and

X and Y are independently selected from =O and =S.

2. A compound according to claim 1, wherein each R$^1$ is independently selected from —OR$^3$; —C(O)OR$^3$; and —C(R$^3$)(R$^4$)—C(O)OR$^3$; and R$^3$ and R$^4$ are independently selected from hydrogen and alkyl.

3. A compound according to claim 1, wherein:

Each R$^1$ is selected from —OR$^3$; —C(O)OR$^3$; and —C(R$^3$)(R$^4$)—C(O)OR$^3$; and R$^3$ and R$^4$ are independently selected from hydrogen and alkyl.

4. A compound according to claim 1, having the general formula (II):

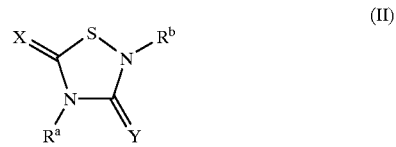
(II)

wherein:

R$^a$ and R$^b$ are independently selected from haloalkyl, —OR$^3$, —C(O)R$^3$, —C(O)OR$^3$, —(Z)$_n$—C(O)OR$^3$, and —S(O)$_t$—, and Z, n, t, R$^3$, R$^4$, X and Y are as defined in claim 1.

5. A compound according to claim 4, wherein R$^a$ and R$^b$ are independently selected from —OR$^3$; —C(O)OR$^3$; and —C(R$^3$)(R$^4$)—C(O)OR$^3$; and R$^3$ and R$^4$ are independently selected from hydrogen, and alkyl.

6. A compound according to claim 5, wherein R$^a$ and R$^b$ are independently —CH$_2$—C(O)OR$^3$; and R$^3$ is hydrogen or alkyl.

7. A compound according to claim 6, wherein R$^a$ and R$^b$ are independently —CH$_2$—C(O)O-ethyl.

8. A compound according to claim 4, wherein X is =O.

9. A compound according to claim 8, wherein X is =O and Y is =O.

10. A compound according to claim 4, wherein:

R$^a$ and R$^b$ are independently selected from —OR$^3$; —C(O)OR$^3$; and —C(R$^3$)(R$^4$)—C(O)OR$^3$;

R$^3$ and R$^4$ are independently selected from hydrogen and alkyl; and

X is =O.

11. A compound according to claim 10, wherein:

R$^a$ and R$^b$ are —CH$_2$—C(O)O-ethyl;

X is =O; and

Y is =O.

12. A pharmaceutical composition comprising a compound having formula (I) as an active ingredient and a pharmaceutically acceptable carrier or diluent:

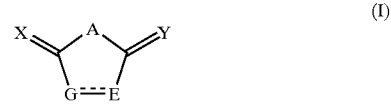
(I)

wherein:

A is —NR$^1$—;

E is —NR¹—;

G is —S—;

- - - is absent;

each R¹ is independently selected from hydrogen, alkyl, cycloalkyl, haloalkyl, aryl, —(Z)$_n$-aryl, —OR³, —C(O)R³, —C(O)OR³, —(Z)$_n$—C(O)OR³, and —S(O)$_t$—;

Z is independently selected from —C(R³)(R⁴)—, —C(O)—, —O—, —C(=NR³)—, —S(O)$_t$— and N(R³)—;

n is zero, one, or two;

t is zero, one, or two;

R³ and R⁴ are independently selected from hydrogen, alkyl, and aryl; and

X and Y are independently selected from =O and =S.

13. The compound of claim 4, wherein the compound is:

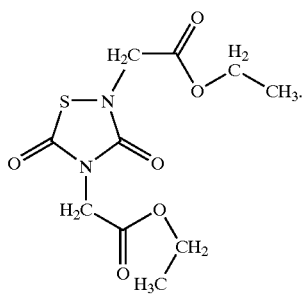

14. The composition of claim 12, wherein the compound is a compound having formula (II):

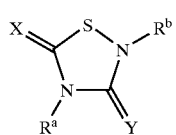

(II)

wherein:

R$^a$ and R$^b$ are independently selected from hydrogen, alkyl, cycloalkyl, haloalkyl, aryl, —(Z)$_n$-aryl, —OR³, —C(O)R³, —C(O)OR³, —(Z)$_n$—C(O)OR³ and —S(O)$_t$—, and Z, n, t, R³, R⁴, X, and Y are as defined in claim 12.

15. The composition of claim 12, wherein each R¹ is independently selected from cycloalkyl; aryl optionally substituted with a group selected from alkyl, halo and alkoxy; —C(R³)(R⁴)-aryl, wherein the aryl part is optionally substituted with a group selected from alkyl, halo and alkoxy; —OR³; —C(O)OR³; and —C(R³)(R⁴)—C(O)OR³; and R³ and R⁴ are independently selected from hydrogen and alkyl.

16. The composition of claim 12, wherein:

each R¹ is selected from hydrogen; alkyl; cycloalkyl; aryl optionally substituted with a group selected from alkyl, halo and alkoxy; —C(R³)(R⁴)-aryl, wherein the aryl part is optionally substituted with a group selected from alkyl, halo and alkoxy; —OR³; —C(O)OR³; and —C(R³)(R⁴)—C(O)OR³; and R³ and R⁴ are independently selected from hydrogen and alkyl.

17. The composition of claim 14, wherein R$^a$ and R$^b$ are independently selected from hydrogen; alkyl; cycloalkyl; aryl optionally substituted with a group selected from alkyl, halo and alkoxy; —C(R³)(R⁴)-aryl, wherein the aryl part is optionally substituted with a group selected from alkyl, halo and alkoxy; —OR³; —C(O)OR³; and —C(R³)(R⁴)—C(O) OR³; and R³ and R⁴ are independently selected from hydrogen, and alkyl.

18. The composition of claim 17, wherein R$^a$ and R$^b$ are independently selected from alkyl; aryl optionally substituted with a group selected from alkyl, halo and alkoxy; —CH$_2$-aryl, wherein the aryl part is optionally substituted with a group selected from alkyl, halo and alkoxy; and —CH$_2$—C(O)OR³; and R³ is hydrogen or alkyl.

19. The composition of claim 18, wherein R$^a$ and R$^b$ are independently selected from methyl; ethyl; propyl; benzyl; phenyl optionally substituted with a group selected from methyl, fluoro, chloro, bromo and methoxy; and —CH$_2$—C(O)O-ethyl.

20. The composition of claim 14, wherein X is =O.

21. The composition of claim 20, wherein X is =O and Y is =O.

22. The composition of claim 14, wherein:

R$^a$ and R$^b$ are independently selected from hydrogen; alkyl; cycloalkyl; aryl optionally substituted with a group selected from alkyl, halo and alkoxy; —C(R³)(R⁴)-aryl, wherein the aryl part is optionally substituted with a group selected from alkyl, halo and alkoxy; —OR³; —C(O)OR³; and —C(R³)(R⁴)—C(O)OR³;

R³ and R⁴ are independently selected from hydrogen and alkyl; and

X is =O.

23. The composition of claim 22, wherein:

R$^a$ and R$^b$ are independently selected from methyl; ethyl; propyl; benzyl; phenyl optionally substituted with a group selected from methyl, fluoro, chloro, bromo and methoxy; and —CH$_2$—C(O)O-ethyl;

X is =O; and

Y is =O.

24. The composition of claim 14, wherein the compound is:

| R$^a$ | R$^b$ | X | Y |
|---|---|---|---|
| CH$_2$Ph | CH$_2$Ph | O | O. |

25. The composition of claim 14, wherein the compound is:

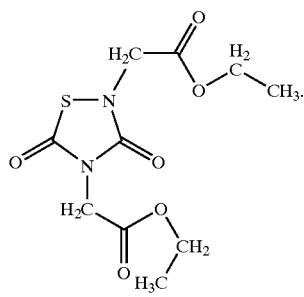

* * * * *